United States Patent [19]

D'Alessio et al.

[11] Patent Number: 5,259,587
[45] Date of Patent: Nov. 9, 1993

[54] ROLLER CLAMP

[75] Inventors: Lawrence D'Alessio, Manasquan; Marvin Gordon, East Windsor, both of N.J.

[73] Assignee: Whitman Medical Corporation, Clark, N.J.

[21] Appl. No.: 895,041

[22] Filed: Jun. 8, 1992

[51] Int. Cl.$^5$ .............................................. F16K 7/00
[52] U.S. Cl. ........................................ 251/4; 251/9; 251/297
[58] Field of Search .................... 251/4, 7, 9, 297

[56] References Cited

U.S. PATENT DOCUMENTS

| | | | |
|---|---|---|---|
| 1,914,851 | 6/1933 | Fyfe | 251/4 |
| 3,016,915 | 1/1962 | Moeller, Jr. | 251/9 X |
| 3,215,394 | 11/1965 | Sherman | 251/4 |
| 3,289,999 | 12/1966 | Konzak | 251/297 X |
| 3,332,439 | 7/1967 | Burke . | |
| 3,533,439 | 10/1970 | Hall . | |
| 3,630,481 | 12/1971 | McGay . | |
| 3,635,472 | 12/1971 | Rychlik . | |
| 3,685,787 | 8/1972 | Adelberg . | |
| 3,802,463 | 4/1974 | Dabney . | |
| 3,893,468 | 7/1975 | McPhee . | |
| 3,900,184 | 8/1975 | Burke et al. . | |
| 3,918,675 | 11/1975 | Forberg . | |
| 3,960,149 | 6/1976 | Bujan . | |
| 3,984,081 | 10/1976 | Hoganson . | |
| 4,013,263 | 3/1977 | Adelberg . | |
| 4,047,694 | 9/1977 | Adelberg . | |
| 4,065,093 | 12/1977 | Phillips . | |
| 4,238,108 | 12/1980 | Muetterties . | |
| 4,270,725 | 6/1981 | Scott et al. . | |
| 4,285,492 | 9/1981 | Bujan . | |
| 4,307,868 | 12/1981 | Morin . | |
| 4,320,889 | 3/1982 | Genese . | |
| 4,335,866 | 6/1982 | Bujan . | |
| 4,337,791 | 7/1982 | Tech et al. . | |
| 4,340,201 | 7/1982 | Becker, Jr. . | |
| 4,373,524 | 2/1983 | Leibinsohn . | |
| 4,390,017 | 6/1983 | Harrison et al. . | |
| 4,406,440 | 9/1983 | Kulle et al. . | |
| 4,463,928 | 8/1984 | Ueda . | |
| 4,475,709 | 10/1984 | Becker, Jr. . | |
| 4,553,963 | 11/1985 | Young . | |
| 4,662,599 | 5/1987 | Attermeier . | |
| 4,688,753 | 8/1987 | Tseng et al. . | |
| 4,697,785 | 10/1987 | Tuseth . | |
| 4,725,037 | 2/1988 | Adelberg . | |
| 4,786,028 | 11/1988 | Hammond . | |
| 4,787,406 | 11/1988 | Edwards et al. . | |
| 4,856,755 | 8/1989 | Clarke . | |
| 4,869,457 | 9/1989 | Ewerlof . | |
| 4,869,721 | 9/1989 | Karpisek . | |
| 4,895,340 | 1/1990 | Forberg . | |
| 4,911,399 | 3/1990 | Green . | |
| 4,919,389 | 4/1990 | Hoekwater et al. . | |
| 4,947,811 | 8/1990 | Binford . | |
| 5,014,962 | 5/1991 | Adelberg . | |

*Primary Examiner*—John C. Fox
*Attorney, Agent, or Firm*—Jacobson, Price, Holman & Stern

[57] ABSTRACT

A tube clamp particularly for adjusting liquid flow through tubes such as I.V. tubes has a channel-shaped holder along which the tube is passed and a rotary eccentric mounted in fixed position between opposite side walls of the holder for applying adjustable pressure on the tube dependent on the rotary position of the eccentric. A ratchet wheel with a spring detent is attached to the eccentric for rotating the eccentric and positively retaining it in a selected position of rotation.

8 Claims, 1 Drawing Sheet

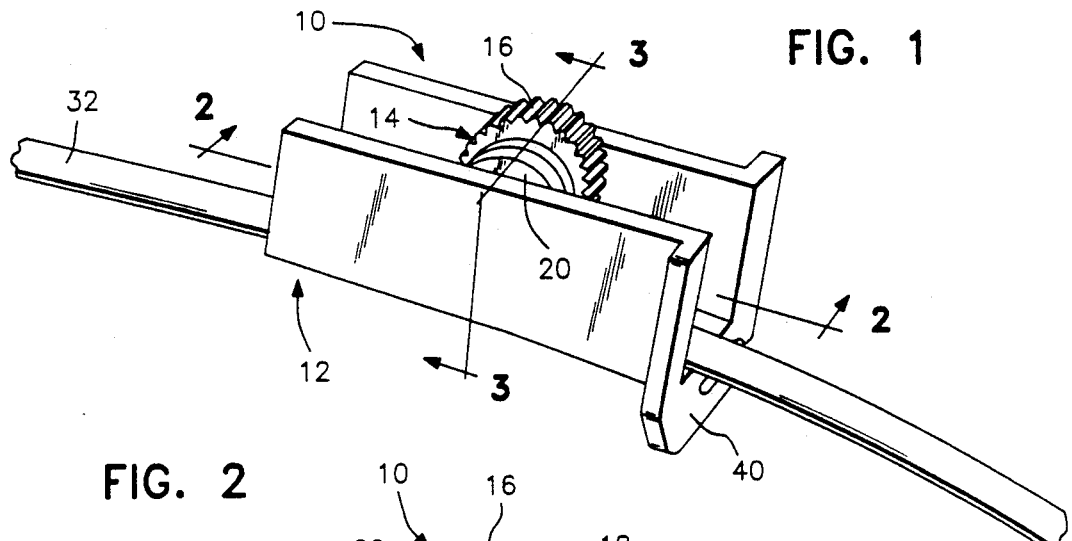
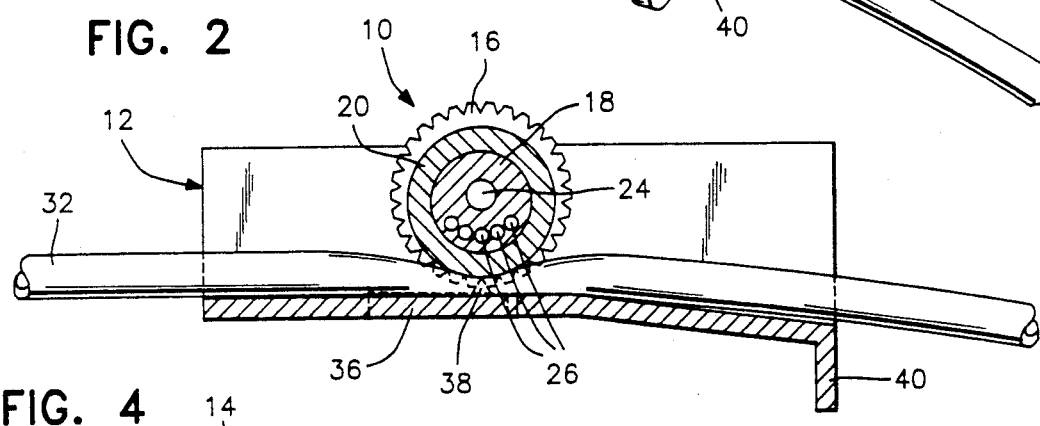
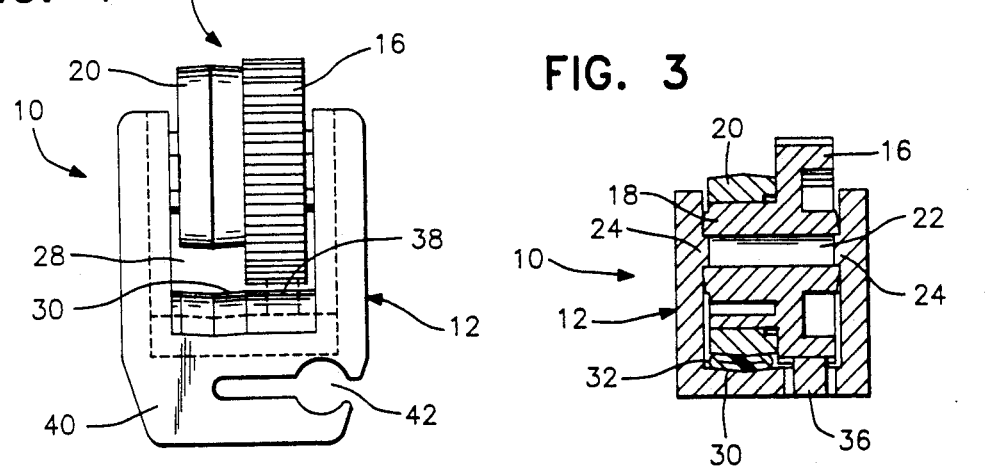
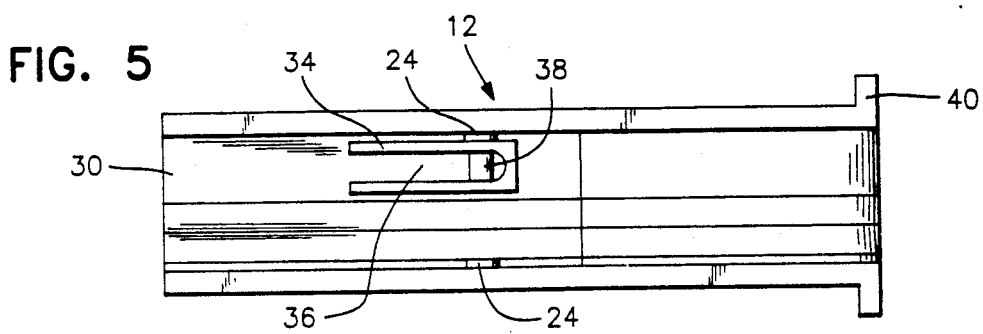

ROLLER CLAMP

BACKGROUND OF THE INVENTION

This invention relates to a roller clamp used to control liquid flow through a flexible tube. The invention finds particular application in the medical field for controlling flow, for example, through I.V. tubing.

It is important accurately to control the flow of I.V. fluid to a patient and this is commonly achieved by means of an adjustable clamp on tubing which delivers the fluid to the patient from an I.V. bag or the like. In use, the clamp is opened or closed on the tube to control the rate of flow.

The prior art is replete with different designs of tube clamps for the above purpose. One common form of clamp comprises an elongate channel-like housing in which is mounted a wheel or roller on an inclined track which extends lengthwise of the channel. The tubing is clamped between the wheel and the base of the channel, and the flow rate through the tubing is varied by moving the wheel along the inclined track so as to increase or decrease its distance from the base of the channel thereby adjusting the degree to which the wheel exerts pressure on the tubing.

Tubing clamps of the above kind may suffer certain disadvantages namely, because of the linear motion of the wheel along the channel to adjust the flow rate, there may not be a positive positioning of the wheel and should the clamp inadvertently be moved along the tube, the flow rate may be altered.

The present invention, therefore, seeks to provide an improved tubing clamp generally of the above type.

SUMMARY OF THE INVENTION

It is an object of the invention to provide a tubing clamp of the kind described comprising a channel-shaped holder and a clamping roller wherein the roller can be positively set in a desired position of adjustment relative to the tubing and only adjusted by intent.

Another object of the invention is to provide a tubing clamp in which the adjusted flow rate will not be altered even if the clamp is moved along the tube.

Still another object of the invention is to provide a tubing clamp which is economical to manufacture and which can be easily positioned on a tube and removed when required.

The above and other objects are achieved in a three-piece roller clamp according to the invention comprising a channel-shaped holder, a ratchet wheel with an integral eccentric hub, and a sleeve-like roller which fits on the hub, all of the components conveniently being plastic moldings.

The ratchet wheel and hub, with attached roller, are adapted to snap into position between opposite walls of the holder for rotation about a fixed axis with no linear motion of the wheel and roller along the channel, and a tube to be clamped is positioned along the base of the holder under the roller. As the ratchet wheel assembly is rotated, the eccentric hub and roller change position relative to the tube so as to close or open the tube and control the flow of liquid through the tube without any linear movement of the wheel.

Preferably, the base of the channel may be formed with a spring detent to engage the serrations of the ratchet wheel, so as to positively retain the wheel and hub in a selected position and allow the setting to be altered only by intent. The roller moreover is preferably free to rotate on the eccentric hub, so that movement of the clamp along the tube is accommodated without altering the adjusted position of the ratchet wheel.

The outer surface of the roller may be bevelled and the base of the channel wherein it receives the tube may be correspondingly shaped so as to ensure that pressure is applied to the tube evenly over its entire cross-section to eliminate voids in the liquid flow and provide constant flow.

The inventive clamp is conceived to be more positive and accurate in flow control than those in current use. Additional features and advantages of the invention will become apparent from the ensuing description and claims read in conjunction with the attached drawings.

BRIEF DESCRIPTION OF THE DRAWINGS

FIG. 1 is a perspective view of a roller clamp according to the invention,

FIG. 2 is a sectional view on line 2—2 of FIG. 1,

FIG. 3 is a sectional view on line 3—3 of FIG. 1,

FIG. 4 is an end view of the roller clamp, and

FIG. 5 is a plan view of a holder element of the roller clamp.

DESCRIPTION OF PREFERRED EMBODIMENT

The illustrated roller clamp 10 comprises a channel shaped holder 12, an element 14 formed by a serrated ratchet wheel 16 and an integral eccentric hub 18, and a sleeve-like roller 20 to fit on the hub. All of these items are conveniently plastic moldings.

Element 14 has a through-bore 22 concentric with ratchet wheel 16, and the hub 18 is eccentric relative to the through-bore. The through-bore enables the element 14 to be rotatably mounted on stub-axles 24 on the opposite side walls of holder 12, the element snap fitting into place, with roller 20 being a loose fit on the hub. Apertures 26 in the hub reduce its weight.

As best seen in FIG. 4, a space 28 is formed between the roller 20 and base wall 30 of the holder, for a flexible tube 32 to pass through, the height of such space being adjustable by virtue of the eccentricity of the hub 18 through rotation of wheel 16 so as to adjust the pressure on, and thereby the flow of liquid through tube 32. Also as best seen in FIG. 4, the outer surface of roller 20 has a convex bevel and base wall 30 of the holder under the roller has a corresponding concave bevel so that the roller applies pressure evenly across the entire width of tube 32.

That part of the base wall 30 of the holder which is under the ratchet wheel has a U-shaped cut-out 34 forming a spring arm 36 with an upstanding detent 38 which engages the teeth of the ratchet wheel. Thus, the ratchet wheel, eccentric hub and roller are positively held in position and the setting of the hub and roller is only altered by the intentional application of rotation to the ratchet wheel. Due to the loose fit of the roller on the hub, movement of the clamp along the tube can be accommodated without altering the adjustment setting of the clamp. At one end the holder has the customary flange 40 with a tube locating cut-out 42.

While only a preferred embodiment of the invention has been described herein in detail, the invention is not limited thereby and modifications can be made within the scope of the attached claims.

We claim:

1. A tube clamp comprising a channel-shaped holder having a base wall and side walls, a rotary member, means mounting said rotary member for rotation about an axis extending between said side walls, said axis being fixed lengthwise of the holder, said rotary member having an outer periphery eccentrically disposed in relation to said axis for applying clamping pressure on a tube extending lengthwise along the base wall of the holder under the rotary member, said pressure being adjustable by rotation of the rotary member, and an operating wheel associated with the rotary member for manually rotating the rotary member, said wheel being positioned between said side walls adjacent the rotary member, said wheel having peripheral serrations and the holder having a spring detent engaging said serrations for positively retaining the wheel and the rotary member in a selected rotary position, said spring detent comprising a spring arm in the base wall of the holder with a detent at a free end of the arm.

2. A tube clamp as claimed in claim 1 wherein the arm is formed by a U-shaped cut-out in the base wall.

3. A tube clamp as claimed in claim 1 wherein the rotary member comprises a hub integral with said wheel and a sleeve-shaped roller positioned over the hub with a loose fit.

4. A tube clamp as claimed in claim 3 wherein the roller and the base wall of the holder have complimentary convex and concave cross-sectional profile portions for applying pressure substantially evenly across the width of the tube.

5. A tube clamp comprising a channel-shaped holder having a base wall and side walls, a rotary member, means mounting said rotary member for rotation about an axis extending between said side walls, said axis being fixed lengthwise of the holder, said rotary member having an outer periphery eccentrically disposed in relation to said axis for applying clamping pressure on a tube extending lengthwise along the base wall of the holder under the rotary member, said pressure being adjustable by rotation of the rotary member, and an operating wheel associated with the rotary member for manually rotating the rotary member, said wheel being positioned between said side walls adjacent the rotary member, said rotary member including an eccentric hub integral with the wheel, and further includes a sleeve-shaped roller fitted loosely over the hub.

6. A tube clamp as claimed in claim 5 wherein the wheel has peripheral serrations and the holder has a spring detent engaging said serrations for positively retaining the wheel and the rotary member in a selected rotary position.

7. A tube clamp as claimed in claim 5 wherein the wheel has peripheral serrations and the holder has a spring detent engaging said serrations for positively retaining the wheel and the rotary member in a selected rotary position.

8. A tube clamp as claimed in claim 5 wherein the wheel has peripheral serrations and the base wall of the holder includes a spring detent arm engaging the serrations and positively retaining the wheel and rotary member in a selected position of rotation.

* * * * *